Figure 1:
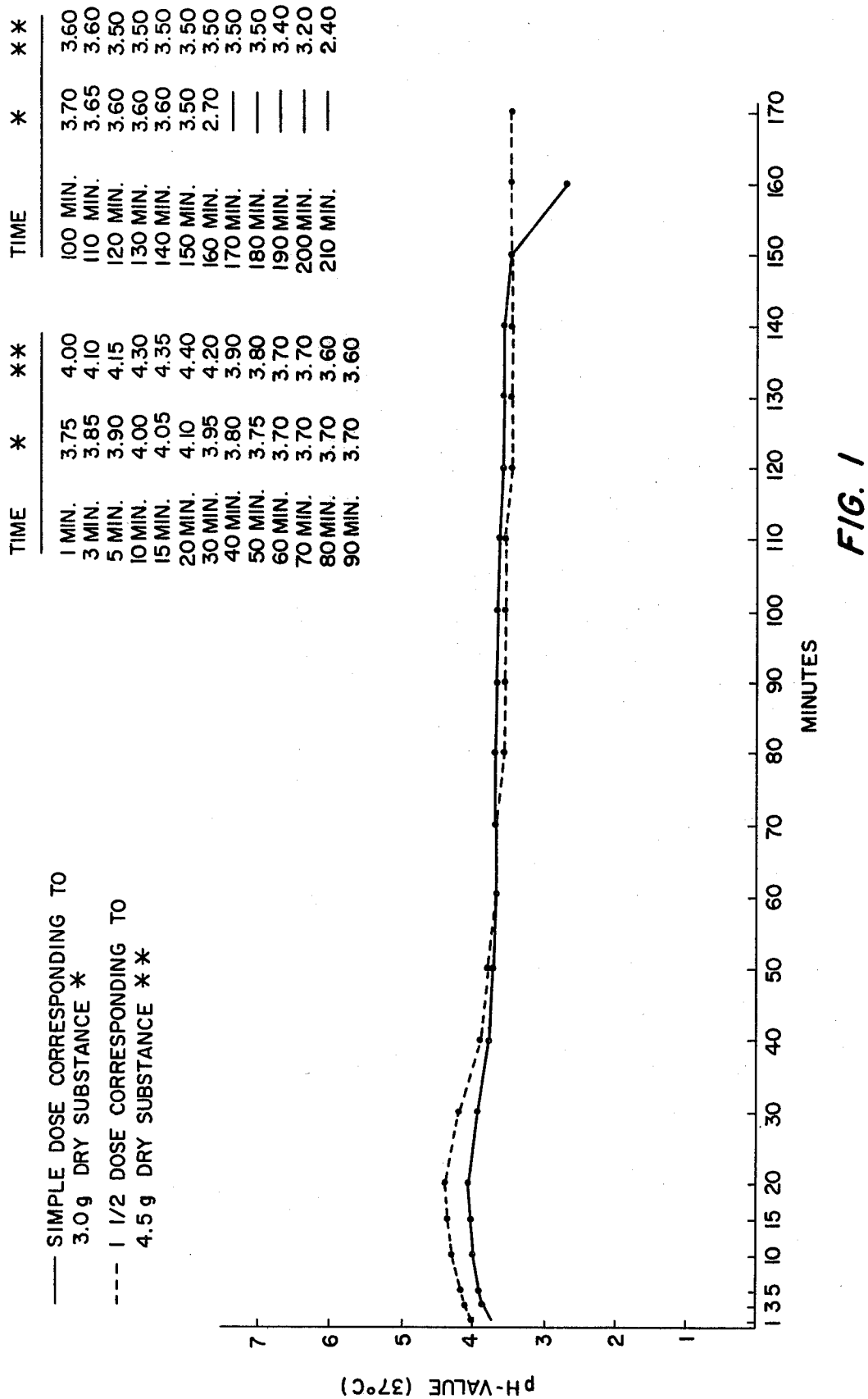

United States Patent [19]

Knecht et al.

[11] 4,443,433

[45] Apr. 17, 1984

[54] ANTACID MATERIAL BASED ON MAGNESIUM ALUMINUM HYDROXIDE AND PREPARATION THEREOF

[75] Inventors: Adolph Knecht; Michael Schneider, both of Freiburg; Walter Ambrosch, Emmendingen, all of Fed. Rep. of Germany

[73] Assignee: Warner-Lambert Company, Morris Plains, N.J.

[21] Appl. No.: 438,104

[22] Filed: Nov. 1, 1982

[30] Foreign Application Priority Data

Nov. 13, 1981 [DE] Fed. Rep. of Germany ....... 3145163

[51] Int. Cl.$^3$ .................... A61K 33/08; C01D 5/10
[52] U.S. Cl. .................... 424/157; 423/518
[58] Field of Search ............... 424/157; 423/600, 629, 423/115, 518

[56] References Cited

U.S. PATENT DOCUMENTS 3,245,876  4/1966  Martin .................... 424/157
3,395,221  7/1968  Snyder et al. .................... 424/157

OTHER PUBLICATIONS

*Chemical Abstracts,* vol. 83, (1975), 84853e.

*Primary Examiner*—Frederick E. Waddell
*Attorney, Agent, or Firm*—Ronald A. Daignault

[57] ABSTRACT

The present invention provides a process for the preparation of an antacid material based upon magnesium aluminium hydroxide, wherein magnesium hydroxide and/or magnesium oxide is reacted in an atomic ratio of magnesium to aluminium of 1:1 to 3:1 with an aqueous solution of aluminium sulphate until the pH of the reaction mixture is from 4.0 to 8.0, whereafter water-soluble components are removed from the mixture in a known manner and the mixture is isolated and, if desired, dried or preferably the mixture obtained after centrifuging or filtering off is used without further purification and optionally dried.

The present invention also provides pharmaceutical compositions containing an antacid material prepared by these processes, in admixture with a conventional pharmaceutical adjuvant.

Furthermore, the present invention provides a method of combating hyperacidity and gastrointestinal diseases, which comprises administering an antacid material prepared by the above processes.

5 Claims, 3 Drawing Figures

ANTACID MATERIAL BASED ON MAGNESIUM ALUMINUM HYDROXIDE AND PREPARATION THEREOF

The present invention is concerned with an antacid material based on magnesium aluminium hydroxide and with the preparation thereof.

Aluminum and magnesium hydroxides, especially in gel form, have proved to be effective antacids in the treatment of gastric hyperacidity and of ulcers.

However, the preparation of a practically useful antacid based upon aluminium magnesium hydroxide comes up against considerable difficulties since a large variety of influences have a negative effect upon the effectiveness or compatibility. An excess, in the physiological sense, of magnesium hydroxide, for example, gives rise not only to a rapid increase of the pH value of the gastric juice above the neutral point and thus induces a rebound effect, i.e. a really excessive production of acid, but also exerts a strongly laxative action. An excess of aluminium hydroxide, on the other hand, usually gives rise to undesirable constipation.

In the case of conventional precipitation methods, bases, for example sodium hydroxide, are also employed, the cations of which cannot be completely removed from the voluminous gels by washing out and, consequently, these cations manifest their own undesired actions. However, sodium ions in particular must not be present in cases of high blood pressure and of diseases of the kidney and heart.

Because of the harmful effects of sodium ions, an attempt has been made, according to U.S. Pat. No. 4,105,579, to obtain aluminium hydroxide gel in pure form by precipitation from aluminium salts with an aqueous solution of magnesium carbonate and subsequent filtration. In this manner, it is admittedly possible to obtain a sodium-free aluminium hydroxide gel but, for the above-mentioned reasons, it cannot be used directly as an antacid but must be admixed with a proportion of magnesium hydroxide.

According to Federal Republic of Germany Patent Specification No. 2,327,768, aqueous ammonia is used as a precipitation agent for the preparation of aluminium hydroxide. However, this process only apparently solves the problem since ammonium ions are also physiologically undesirable and, in the same way as alkali metal ions, are stubbornly held by the gel.

As is also known from Federal Republic of Germany Patent Specification No. 1,617,277 (column 2, lines 55–63), it is extremely difficult to dry aluminium and magnesium hydroxide gels without their losing a considerable part of their acid-binding activity. In the case of aluminium hydroxide gels, this disadvantage is even regarded as being a characteristic.

It is an object of the present invention to provide an antacid material which, apart from aluminium and magnesium, does not contain any other cations and, in a dry state, even after storage for a comparatively long time, does not lose its acid-binding buffer capacity and which has an extraordinarily long period of action without leaving the ideal buffer range of from about pH 3 to pH 5 during any period of treatment in that solid magnesium hydroxide and/or magnesium oxide is used as a precipitating agent for aluminium hydroxide from a solution of aluminium sulphate [$Al_2(SO_4)_3$] in water and the product obtained, after the removal of water-soluble components, is isolated in a known manner and, if desired, dried. The starting materials are used in an atomic ratio of Mg:Al of 1:1 to 3:1 and preferably of from 1.3:1 to 2:1. The precipitation reaction is finished when the reaction mixture has reached a pH value in the range of from 4.0 to 8.0, preferably of from 5.0 to 7.0. However, it is possible to go slightly above or below the stated ranges but this is not advantageous.

According to U.S. Pat. No. 3,239,416, an attempt has already been made to react a basic aluminium chloride [$Al_2(OH)_2Cl_4$ or $Al_2(OH)_5Cl$] with appropriate non-toxic alkaline earth metal compounds. However, due to the presence of hydroxyl groups in the aluminium complex, a cross-linking in the end product is only partly possible. Consequently, a gel-like precipitate, a so-called co-gel, is obtained, the properties of which differ considerably from those of the end product obtained according to the present invention and which, in addition, must be freed from undesired chloride ions by repeated and laborious washing. Furthermore, in order to achieve a suitable pH value for the reaction, the addition of sodium carbonate or sodium bicarbonate is usually necessary when carrying out this known process.

A similar proposal, which by-passes the object of the present invention, has also been disclosed in Chemical Abstracts, 83, 84853e/1975. In this case, too, a prehydrolysed polybasic aluminium sulphate of limited reactivity is reacted with magnesium hydroxide. Due to the hydrolysis with sodium bicarbonate, undesired sodium ions are entrained which can be removed from the resultant gel only with difficulty.

In U.S. Pat. No. 4,105,579, a process is described for the preparation of a more or less pure aluminium hydroxide by precipitation from aluminium chloride solutions (or, alternatively, also nitrate and sulphate) by means of an alkaline earth metal carbonate, undesired amounts of carbonate thereby getting into the end product.

Therefore, according to the present invention, there is provided a process for the preparation of an antacid material based upon magnesium aluminium hydroxide, wherein magnesium hydroxide and/or magnesium oxide is reacted in an atomic ratio of magnesium to aluminium of 1:1 to 3:1 with an aqueous solution of aluminium sulphate until the pH of the reaction mixture is from 4.0 to 8.0, whereafter water-soluble components are removed from the mixture in known manner and this is isolated and, if desired, dried.

After complete removal of the readily water-soluble components, a product is obtained with the following properties:

1. the atomic ratio of aluminium to magnesium is from 0.5:1 to 7:1 and preferably from 1:1 to 6:1;
2. the pH value of an aqueous suspension thereof is from 5.5 to 9.0 and preferably from 6.0 to 8.5;
3. a dose of the product prepared according to the present invention with 20 mMol aluminium reaches, in the case of the determination of the acid-binding capacity by Schaub's method (see Pharm. Acta Helv., 38, 16/1963), a pH value of 3.5 after only 1 minute. In most cases, the pH value does not exceed 4.5 and in all cases it is below 5.0 and, in spite of the addition of Schaub's simulated gastric juice, it remains above pH 3.0 for at least 120 minutes and, in many cases, for up to 160 minutes;
4. the active material obtained only contains the physiologically compatible cations present in the starting materials and, as anions, only contains sulphate and hydroxyl ions and is, therefore, also suitable for high-dosage antacid and for long-term therapy.

Thus, according to the present invention, it is possible, with very simple agents and without the use of foreign additives, to prepare a highly effective antacid material which, according to present day knowledge, displays an ideal activity profile. In particular, it possesses the following properties which are demanded of an ideal antacid and is, therefore, superior to the known antacids:

1. the action commences immediately without an increased gastric acid secretion and a rebound effect resulting due to exceeding the admissible limit of pH 5;
2. the buffering of the gastric juice within the narrow ideal range of from pH 3 to pH 5 is maintained for at least 2 hours;
3. the antacid reduces the pepsin activity without, however, completely inhibiting it;
4. the antacid does not have any harmful side effects since the magnesium and aluminium ions are in a balanced ratio to one another and no undesired foreign cations, such as sodium, calcium, ammonium, bismuth and the like, and no undesired anions, such as chloride, carbonate and the like, are present;
5. the antacid also binds bile acids which play a part in the genesis of haemorrhagic gastritis and of ulcers;
6. the active material is stable, also retains its buffer capacity in dry form for a long time and has a completely neutral taste;
7. a safe preservation for the avoidance of microbial growth is possible in suspensions of this antacid material because of its optimum pH range;
8. in contradistinction to known gels, the antacid is obtained in the form of a powder which can be easily filtered or centrifuged and can also be very readily further worked up.

The process of preparation according to the present invention gives a hydroxide mixture or a hydroxide/oxide mixture in which the strong basicity of the magnesium hydroxide or oxide component is initially fully masked by the aluminium hydroxide gel precipitated from the solution so that this only acts slowly.

This leads to a previously unachieved flattening of the pH curve of the gastric juice which, in the case of the known hydroxide mixtures, always displays, shortly after administration, a distinct maximum above pH 5 but, in the present case, proceeds very flatly and always below pH 5.

A precise chemical analysis of the structure of the antacid material according to the present invention has hitherto not been carried out. However, it is assumed that the sulphate ion, due to its divalency, forms bridges and thus possibly sparingly soluble basic mixed salts, which hold firmly bound a more or less large proportion of the sulphate anions but which are physiologically completely compatible. Whether this proportion of anions is partly responsible for the outstanding physiological properties of the antacid prepared according to the present invention or whether this depends preponderantly upon the heterogenous precipitation method used and a covering of the basic magnesium hydroxide by aluminium hydroxide or by its mixed salts possibly resulting thereby, has not yet been elucidated. However, it has been shown that the sulphate content also positively influences the physical properties, for example easy filterability.

It must be observed that the ideal atomic ratio of aluminium to magnesium depends upon the starting materials. In the case of too great an excess of aluminium salt, the magnesium hydroxide can be completely dissolved; the yield of antacid material is then small and such a fine precipitate is formed that separation thereof becomes difficult. In the case of too great an excess of magnesium hydroxide or oxide, a precipitate is admittedly obtained which can be easily separated but the product then assumes more and more the undesired properties of pure magnesium hydroxide and the kinetics of the acid-binding capacity (according to Schaub) deteriorate. At the commencement of treatment with such an antacid, a pH maximum above pH 5 then distinctly occurs, which is typical for magnesium hydroxide or oxide.

The atomic ratio in the antacid end product is determined by the quantitative atomic ratio of aluminium to magnesium in the starting materials. By the choice of a particular atomic ratio, it is very easy to adjust an atomic ratio of aluminium to magnesium in the antacid end product within the preferred range of from 0.5:1 to 7:1. The particle size of the magnesium hydroxide or magnesium oxide used as starting material is preferably from 10 to 50 $\mu$m.

The amount of water used also has an influence upon the physical properties of the antacid product. In this regard, care should be taken that the concentration of the aluminium sulphate solution and of the magnesium hydroxide or oxide suspension is not too high since the product can otherwise only be filtered off with difficulty. It is preferred to use a 0.2 to 0.3 molar aqueous aluminium sulphate solution and an approximately 1 molar magnesium hydroxide suspension as starting materials.

For the process of preparation, it is immaterial whether the aluminium sulphate in solution is added to a slurry of the magnesium hydroxide or magnesium oxide or whether the reverse procedure is used and the magnesium hydroxide or oxide slurry is introduced into the solution of the aluminium sulphate. However, it is important continuously to monitor the pH value of the reaction mixture after mixing the reaction components together and to stir the mixture until the desired pH value has been obtained.

Since the aluminium content in the end product increases with an increasing period of stirring at the expense of the magnesium content, it is also possible to control the mole ratio to a certain extent by the period of reaction. The acidic pH value in the reaction mixture initially increases very quickly and then asymptotically approaches the end value. For an appropriate quality of the antacid material, the components should be reacted together at least until a pH of from 4 to 8 is reached. The reaction can be accelerated by increasing the temperature, without changing the end product. However, the temperature should not exceed 60° C.

At the end of the reaction, water-soluble magnesium salts are removed by washing out. Even after a single washing of the filtered off antacid material, less than 2% of the dissolved materials (referred to the dried product) are present in the first wash water. The soluble and non-toxic salts are thus removed from the antacid material to such an extent that it can be used directly.

In practice, the product is washed twice at most. The sulphate content of the antacid product, dried for 4 hours at 110° C. is in the range of from 5 to 25% and preferably of from 10 to 20%.

A preferred aspect of the present invention provides that the purification of the mixture obtained above can be omitted, i.e. that the mixture can, without further removal of the water-soluble components, directly after filtering or centrifuging off of the mother liquor, be used, optionally after drying.

Thus, according to the preferred aspect of the present invention, there is provided a process for the production of an antacid active material based on magnesium-aluminium hydroxide, in which magnesium hydroxide and/or magnesium oxide is reacted in an atomic ratio of 1:1 to 3:1 (Mg:Al) with an aqueous solution of aluminium sulphate until the pH value has reached the range of from 4.0 to 8.0 and the mixture obtained is isolated, characterised in that the mixture obtained after centrifuging or filtering off is used without further purification and optionally dried.

It is to be regarded as being extremely surprising that the mixture obtained according to the preferred aspect of the present invention has a substantially higher storage stability than the active material produced after removal of the water-soluble components. In a moist or dry state, the mixture has a considerably higher neutralisation capacity over a long period of storage time. Especially in the case of drying the product by the action of heat, in contradistinction to the washed product and surprisingly no loss of neutralisation capacity occurs. It has also been shown that the flavour impairment is substantially smaller than originally asumed so that the flavour quality of the unpurified product, especially after appropriate galenical working up, is completely satisfactory.

Consequently, the process according to the preferred aspect of the present invention leads not only to an improved end product but also saves an expensive and time-consuming purification process.

With the increased electrolyte content, an aqueous suspension is stabilised.

The avoidance of the purification is also physiologically acceptable since the undesired ions, for example sodium or ammonium, are not present and the higher sulphate content (up to 34% by weight, referred to the twice washed product) having regard to the natural occurrence of sulphates in the secreta of the gastric mucosa, is in no way to be considered in a negative manner.

When carrying out the process of the preferred aspect of the present invention, it is preferable that the starting materials are used in an atomic ratio of magnesium to aluminium of 1.3:1 to 2:1. Furthermore, it is preferable to finish the reaction when the reaction mixture has reached a pH value of from 5.0 to 7.0.

In spite of changing of process, all the other advantages such as are described above are retained.

For the determination of the optimum molar atomic ratio (i.e. in the end product, the longest possible buffering time above pH 3.0 and no increase of the pH value above 5.0 in the case of determining the acid-binding capacity by Schaub's method) of magnesium to aluminium in the starting materials, a series of experiments is carried out. The same amounts of magnesium hydroxide are thereby reacted with increasing amounts of aluminium sulphate under otherwise the same reaction conditions.

The following Table 1 summarises the results of this series of experiments. The experiments were carried out as follows:

2 g. Magnesium hydroxide were suspended in 18 g. of water. Aluminium sulphate octadecahydrate was weighted out in a molar ratio and dissolved in sufficient water to give 80 g. of solution. The solution was then added, with stirring, to the magnesium hydroxide suspension. The reaction mixture was stirred for 3 hours, during which time the pH value of the reaction mixture was continuously measured. The precipitate obtained was filtered off through a G3 frit under reduced pressure and well washed twice with 50 ml. amounts of water. Subsequently, the product was well dried by passing air therethrough. Finally, the antacid product obtained in this manner was examined for its acid-binding capacity by Schaub's method (Pharm. Acta Helvetica, 38, 16/1963). The results of the experiments are given in the following Table 1:

TABLE 1

| Experimental series of $Mg(OH)_2$ with $Al_2(SO_4)_3 \cdot 18H_2O$ | | | | |
|---|---|---|---|---|
| atomic ratio Mg:Al in the starting materials | pH value of the reaction mixture at the end of the reaction | yield after drying 110° C./ 4 hrs. | acid-binding capacity | |
| | | | buffering time above pH 3.0 | pH value peak after 20 minutes |
| 1 Mg:0.60 Al | 6.0 | 2.18 g. | 140 min. | 5.1 |
| 1 Mg:0.65 Al | 6.0 | 2.59 g. | 150 min. | 5.0 |
| 1 Mg:0.70 Al | 5.7 | 2.67 g. | 150 min. | 4.1 |
| 1 Mg:0.75 Al | 5.4 | 2.79 g. | 150 min. | 3.9 |
| 1 Mg:0.80 Al | 4.2 | 3.05 g. | 160 min. | 3.6 |
| 1 Mg:0.85 Al | 4.0 | 2.50 g. | 120 min. | 3.8 |

The atomic ratio was calculated as follows:

2 g. $Mg(OH)_2 = 0.03429$ mol Mg 8 g. $Al_2(SO_4)_3 \cdot 18H_2O = 0.01200$ mol
$Al_2(SO_4)_3 \cdot 18H_2O = 0.02400$ mol Al which corresponds to an atomic ratio in the starting materials of magnsium to aluminium of 1:0.7.

If the amounts of aluminium sulphate are too low, the disadvantageous properties of magnesium hydroxide with regard to acid-binding capacity occur, i.e. the pH value peak is above 5.0

If the amount of aluminium sulphate is too great, the magnesium hydroxide can be completely dissolved and only aluminium hydroxide is present as a gel, which is difficult to filter, or, in extreme cases, only a clear solution is obtained.

The most favourable atomic ratio can be easily determined by evaluation of the values for yield, buffering time and pH value peak. Those atomic ratios are selected within the preferred pH range (pH value peak) with which, in the case of the most favourable yields, there is associated the longest buffering time.

Gel-like aluminium or magnesium hydroxides prepared by precipitation are, because of their structure, extremely difficult to filter. Surprisingly, we have found that the process according to the present invention does not suffer from this disadvantage and, especially in the preferred process ranges, gives a product which is easy to filter and is capable of elution. This is a further considerable technical advantage over the prior art.

The antacid product according to the present invention can, after gentle drying, be worked up directly in known manner to give solid compositions for oral administration, for example capsules, dragees, granulates or, prefrably, tablets. For the production of solid compositions for oral administration, use is made, in the conventional manner, of adjuvant and carrier materials, for example starch, lactose, mannitol, methyl cellulose, talc, highly dispersed silicic acids, high molecular weight fatty acids (for example stearic acid) and the salts or esters thereof, gelatine, agar-agar, animal and vegetable fats and solid high molecular weight polymers (for example polyethylene glycol). If desired, the compositions can also additionally contain flavouring and/or sweetening agents. The composition is preferably so dosed that one dosage unit contains 0.3 to 1.0 g. of antacid product. 1 to 2 Units of this composition can be administered several times a day at intervals of 1 to 2 hours since it is completely non-toxic.

The antacid product according to the present invention is, in a moist or dry state, also outstandingly useful for the production of suspensions, in which case, in addition to the above-mentioned adjuvants, thickening agents and conventional suspension stabilisers are also added. Suspensions are generally the preferred form of administration for antacids, for which reason they are also especially preferred according to the present invention.

The liquid forms of administration can contain, per milliliter, about 0.1 to 0.2 g. of antacid product. There are thus obtained dosage units of about 6 ml., which correspond to one teaspoonful. Here, too, depending upon the severity of the disease picture, 1 to 2 dosage units can be administered at intervals of 1 to 2 hours during the course of the day.

The antacid product according to the present invention can also be worked upon in a moist state as a liquid pharmaceutical form so that drying measures can be omitted.

The active material according to the present invention also possesses the great advantage that it can be preserved with conventional preservation agents which are practically only effective in a weakly acidic to neutral pH range. As described above, aqueous suspensions of the active material are characterised by a weakly acidic to weakly basic pH range, whereas all previously known compositions have, as far as is known, a distinctly basic pH value. Thus, for example, the active material according to the present invention can be preserved in aqueous suspension by, for example, sorbic acid, benzoic acid or PHB ester, which lose their effectiveness in the basic pH region.

For the production of solid pharmaceutical forms, a gentle drying process should be used, i.e., the thermal stressing should be as small as possible. Normally, however, drying is unnecessary since the filter cake, after the addition of the necessary additives, can be directly granulated and further worked up to give tablets.

The following Examples are given for the purposes of illustrating the present invention:

EXAMPLE 1

0.012 mol aluminium sulphate with variable amounts of water of crystallization are dissolved, while stirring in 42 ml. of water, with gentle heating up to about 50° C. 0.034 mol magnesium hydroxide, suspended in 30 ml. of water, are slowly added, with vigorous stirring, to the aluminium sulphate solution. After complete addition of the suspension, the reaction mixture is stirred (about 1 hour) until the aqueous suspension has reached a pH value of 5.5. The mixture is then filtered under reduced pressure through a G3 frit and, with resuspension, washed twice with 50 ml. amounts of water. After filtering off, the precipitate is dried, first at ambient temperature and then for 4 hours at 60° C. The yield is 3.0 g. The pH value of an aqueous suspension of the product is 6.0.
Composition:
  0.02 mol aluminium
  0.005 mol magnesium.
Acid-binding capacity by Schaub's method:
  buffering time (above pH 3.0)=150 minutes
  pH value after 20 minutes=4.1.

Figure 2:
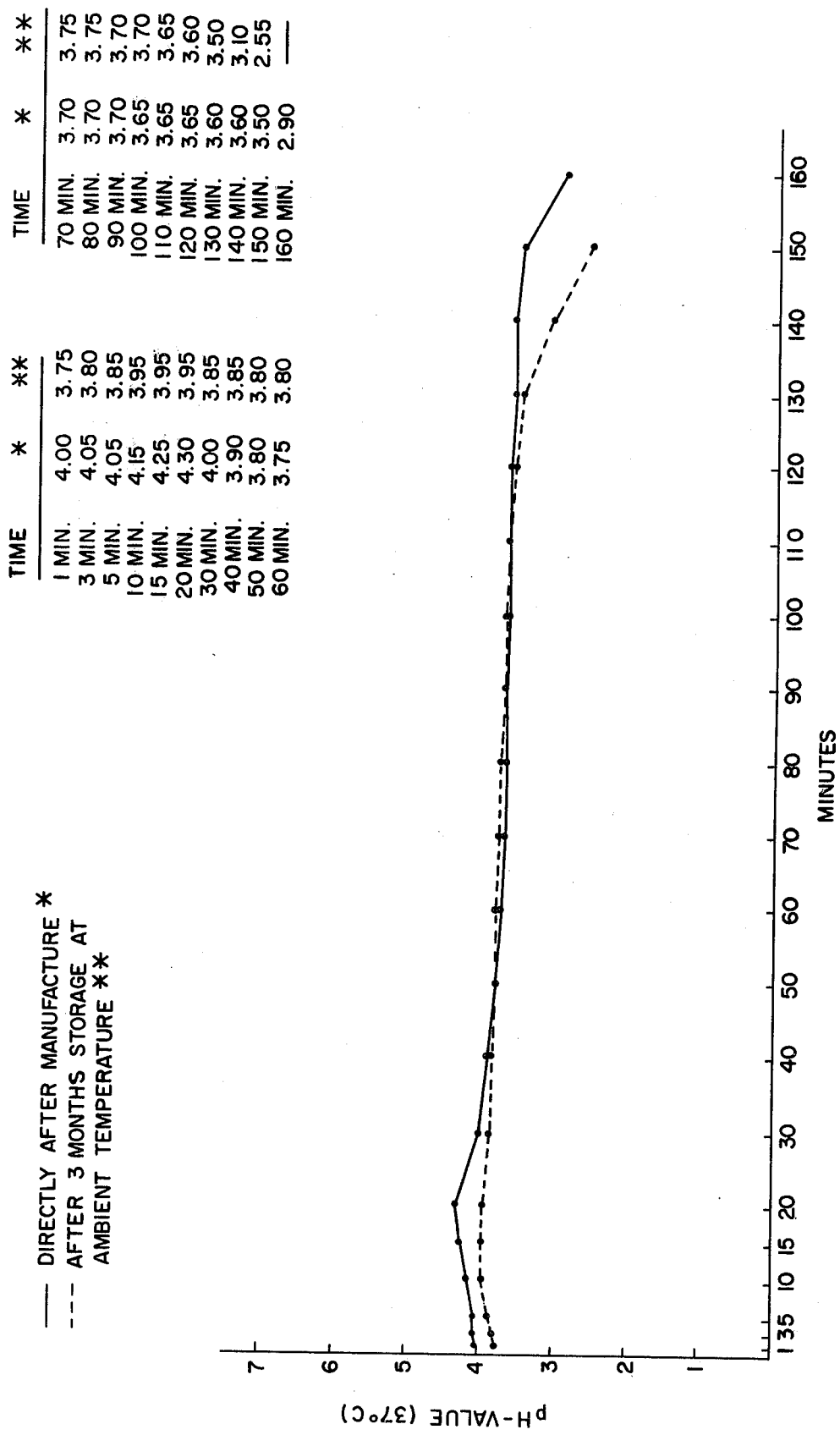

The course of the acid-binding capacity under different conditions is given in FIGS. 1 and 2 of the accompanying drawings.

EXAMPLE 2

1 kg. Magnesium hydroxide is suspended in 14 kg. of water. To this suspension is added a solution, prepared at 60° C., of 4 kg. aluminium sulphate octadecahydrate in 21 liters of water, while stirring. After stirring for 3 hours, the reaction mixture has a pH of 5.8. The reaction mixture is then filtered off under reduced pressure and washed twice, with resuspension, with 15 liter amounts of water and dried in the air. Yield 3.5 kg.

EXAMPLE 3

223 g. Aluminium sulphate octadecahydrate are dissolved in 750 g. of water. Subsequently, 60 g. magnesium hydroxide in pulverized form are sprinkled in, while stirring. Stirring is continued until the reaction mixture has a pH value of 4.7. The precipitate is filtered off under reduced pressure through a G3 glass frit, then well washed twice with about 200 ml. amounts of water and subsequently dried by passing through air. The yield is about 480 g.

EXAMPLE 4

39 g. Magnesium oxide are suspended in 0.5 liters of water. At the same time, 240 g. aluminium sulphate octadecahydrate are dissolved in 0.7 liters of water and subsequently added, while stirring, to the magnesium oxide suspension. The mixture is stirred until a pH value of 4.3 is reached. After washing twice with 200 ml. amounts of water, the product is filtered off and dried at 30° C. The yield is 300 g.

Figure 3:
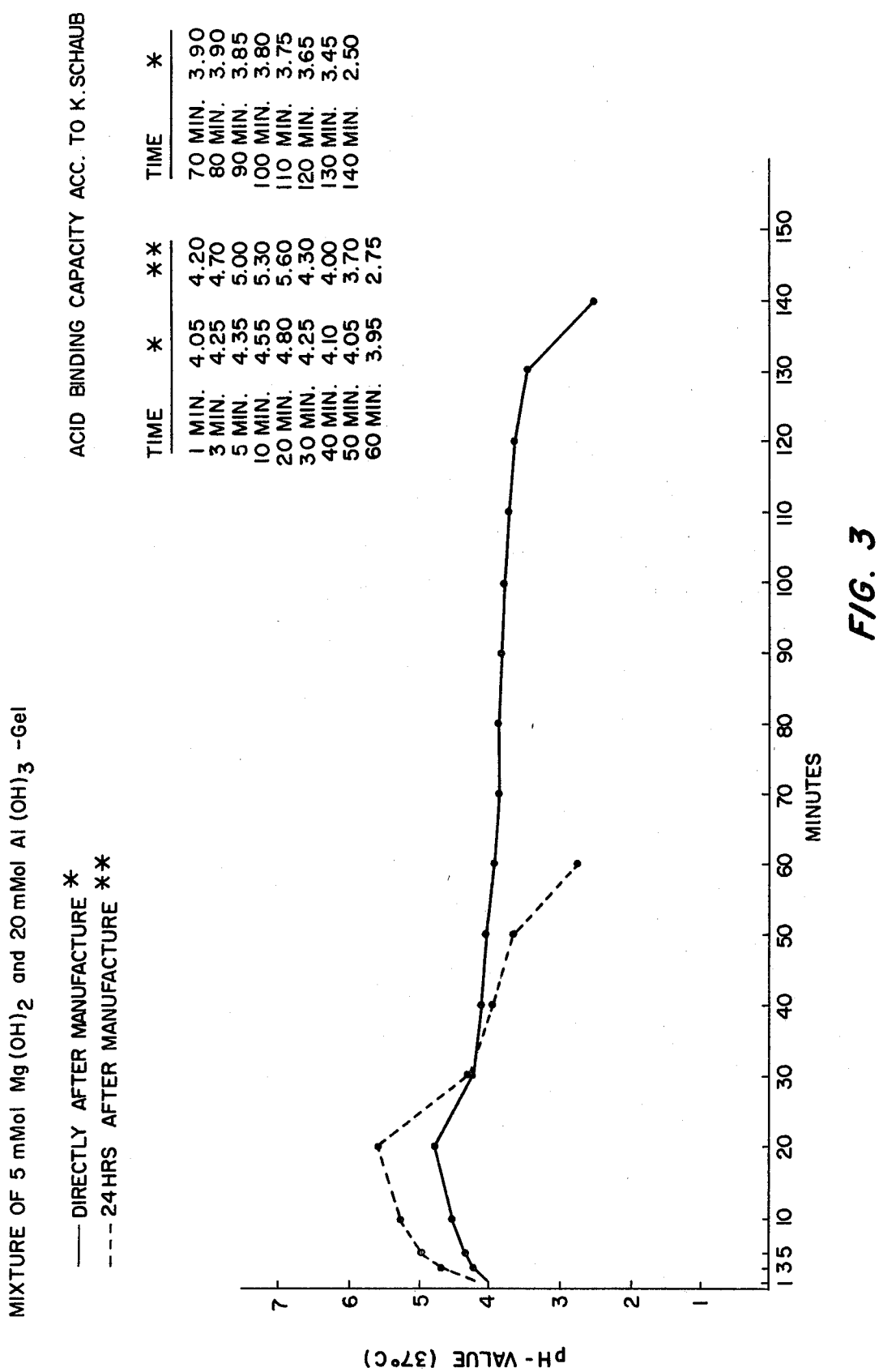

FIGS. 1 to 3 of the accompanying drawings illustrate the acid-binding capacities (by Schaub's method) of the product of Example 1 and of a comparison mixture.

FIG. 1 shows the acid-binding capacity of the product of Example 1 at a dosage of 3 g. and 4.5 g. of dry substance. It can be seen that, after about 15 minutes, a very flat pH maximum of about pH 4.4 is reached which, after a further 15 minutes, runs practically in a straight line. A distinct pH drop can only be seen after about 130 or 180 minutes (Table).

FIG. 2 shows a comparative curve of the product according to Example 1 from which it can be seen that a product stored for 3 months shows only a slight loss of activity.

FIG. 3 shows the course of the curve of the acid-binding capacity of a conventional mixture consisting of 5 mMol magnesium hydroxide and 20 mMol aluminium hydroxide gel. The undesired pH maximum can be clearly seen and, in the case of the preparation which is 24 hours old, the pH of 5 is exceeded after only 5 minutes. It can also be seen that the pH value drops again to below 3 in less than an hour.

EXAMPLE 5

6.75 kg. magnesium hydroxide are suspended in 100 kg. water and 22 kg. aluminium sulphate octadecahydrate are dissolved in 100 kg. water. The aluminium sulphate is slowly added, while stirring, to the magnesium hydroxide suspension. After stirring for 6 hours, the pH value in the reaction mixture increases to 6.7. Subsequently, the reaction mixture is separated from the mother liquor under vacuum by means of a filter funnel and filter bag and the filter cake is dried by air flowing therethrough. One third of this filter cake is separated off and divided into two. One half, while still in a moist state, is worked up to give an aqueous suspension (20%, referred to the dry substance (Part 1.) The other half is dried in racks in a drying cabinet at 50° C. for 4 hours (Part 2). The remaining two thirds of the filter cake are resuspended in 67 kg. of water, stirred for at least 10 minutes and subsequently filtered off under vacuum by means of a filter funnel. The filter cake dried by means of throughflowing air is divided into two. One half of the once washed, still moist filter cake is then divided into two and one half is worked up to give an aqueous suspension (Part 3), whereas the remainder is dried at 50° C. for 4 hours on racks in a drying cabinet (Part 4) and subsequently homogenised and worked up to give an aqueous suspension.

The remainder of the once washed, still moist filter cake is again resuspended in 33 kg. of water, stirred for at least 10 minutes and subsequently filtered off under a vacuum by means of a filter funnel. The filter cake dried by means of through-flowing air is divided into two. One half of the twice washed, still moist filter cake is worked up to give an aqueous suspension (Part 5), whereas the remainder is dried at 50° C. for 4 hours (Part 6), homogenised and worked up to give an aqueous suspension.

The following Table 2 shows that the neutralisation capacity of the product is considerably reduced by washing.

The neutralisation capacity of the suspension is determined by the method of K. H. Holtermuller, E. Bohlen, M. Castro and H. J. Weis (Med. Klin., 72, 1229–1241/1977). The Part 2 of the unwashed antacid substance is, homogenised by sieving (1 mm. mesh size) and mixing. Subsequently, an aqueous suspension thereof is produced and the neutralisation capacity determined.

From the following Table 2, it can be seen that the unwashed portion possesses the greatest neutralisation capacity, the otherwise unfavourable drying process not resulting in any loss of capacity.

The twice washed portion has a considerably lower neutralisation capacity and, after drying, a decrease of up to 20% is observed.

TABLE 2

Influence of washing on the stability behaviour of the antacid substance in the case of drying in a hot air cabinet (50° C./4 hours.), assessed on the basis of the neutralisation capacity

| antacid substance used | neutralisation capacity in ml. 0.1 hydrochloric acid per 1 g. of aqueous suspension (20%, referred to the dry substance) |
| --- | --- |
| unwashed, moist (Part 1) | 55 ml. |
| unwashed, dried (Part 2) | 55 ml. |
| 1 × washed, moist (Part 3) | 55 ml. |
| 1 × washed, dried (Part 4) | 51 ml. |
| 2 × washed, moist (Part 5) | 53 ml. |
| 2 × washed, dried (Part 6) | 46 ml. |

We claim:

1. A process for the preparation of an antacid material based upon magnesium aluminium hydroxide, wherein magnesium hydroxide and/or magnesium oxide is reacted in an atomic ratio of magnesium to aluminium of 1:1 to 3:1 with an aqueous solution of aluminium sulphate until the pH of the reaction mixture is from 4.0 to 8.0 whereafter water-soluble components are removed from the mixture by centrifugation or filtration and the isolated mixture, if desired, dried.

2. A process according to claim 1, wherein the mixture obtained after centrifuging or filtering off is used without further purification and optionally dried.

3. A process according to claim 1, wherein the starting materials are used in an atomic ratio of magnesium to aluminium of 1.3:1 to 2:1.

4. A process according to claim 1 or 3, wherein the reaction is terminated when the pH of the reaction mixture is from 5.0 to 7.0.

5. A process according to claims 1, 3 or 4, wherein the reaction is carried out at a temperature which does not exceed 60° C.

* * * * *